United States Patent [19]

Jones

[11] Patent Number: 4,934,178

[45] Date of Patent: Jun. 19, 1990

[54] METHOD AND APPARATUS FOR DETERMINING THE DENSITY OF A GAS

[76] Inventor: Donald R. A. Jones, 7219 Sorensen Ave., Whittier, Calif. 90606

[21] Appl. No.: 286,146

[22] Filed: Dec. 19, 1988

[51] Int. Cl.$^5$ .......................... G01N 9/26; G01N 9/32
[52] U.S. Cl. .................................... 73/32 R
[58] Field of Search ............ 73/861.61, 861.63, 32 R, 73/1 R

[56] References Cited

U.S. PATENT DOCUMENTS

| | | | |
|---|---|---|---|
| 4,285,245 | 8/1981 | Kennedy | 73/861 |
| 4,527,418 | 7/1985 | Arcara | 73/32 R |
| 4,528,847 | 7/1985 | Halmi | 73/861.61 |
| 4,651,572 | 3/1987 | Albertz et al. | 73/861.63 |

Primary Examiner—John Chapman
Assistant Examiner—Robert P. Bell
Attorney, Agent, or Firm—Bruce L. Birchard

[57] ABSTRACT

The method and apparatus for determining the density of a gas by measuring the time for a predetermined its flow through a sub-sonic square-root restrictor, such as a venturi, the rate of increase or decrease of the pressure in a reference chamber, a semi-continuous measurement means utilizing a motor driven, constant rate-of-movement piston being disclosed as well as a continuous density measurement means including a sub-sonic square-root restrictor followed, in fluid flowing fashion by a sonic restrictor venting to the atmosphere.

3 Claims, 3 Drawing Sheets

METHOD AND APPARATUS FOR DETERMINING THE DENSITY OF A GAS

BACKGROUND OF THE INVENTION

1. Field of the Invention

This invention relates to the measurement of the density of a gas or gas mixture to the end that the mass rate of flow of that gas may be determined accurately and, more particularly, to the method and apparatus for the calibration of gas meters in the field.

2. Prior Art

In the distribution of commercially used gas, such as natural gas, it is necessary, from time-to-time, to calibrate meters which measure the use of gas by commercial or consumer uses. In the past only complex, expensive and heavy equipment (such as the Solartron Model 7810 Densitometer) has been available.

Therefore, it is an object of this invention to provide a method and apparatus which overcome the problems of prior art gas-flow methods and apparatus.

It is a further object of this invention to provide a method which is accurate in the measurement of gas flow and utilizes apparatus which is accurate, lightweight and simple to operate.

SUMMARY OF THE INVENTION

This invention recognizes and utilizes the principle that the sub-sonic mass flow of gas through an orifice having a "square-root" type of flow restriction (a venturi, for example) is a function of the square-root of the density. Thus, the time required for a gas to flow from a closed vessel through a sub-sonic restrictor is dependent upon the density of the gas.

The flow may be inward to a reference chamber or outward therefrom. The necessary element is one or more "square-root" orifice venturi or other "square-root" type of restrictor. Of course, the initial pressure and temperature of the gas in the reference chamber must be known accurately and monitored during the rise or fall of the pressure in the chamber. In the pressure-fall system the chamber must be thoroughly purged with the gas, the flow of which is to be measured, before the method is utilized to determine the density of the commercial gas. In the pressure-rise system, the pressure in the chamber must be reduced to atmospheric pressure before the measurement is begun. In either case the density of the gas is related to the time required for the pressure to change between two predetermined levels. A combination of sub-sonic and sonic venturis may be utilized to achieve a continuous measurement of gas density. With this method the gas flow through the sub-sonic restrictor is proportional to the square-root of the gas density while the flow through the sonic restrictor to which it is coupled is directly proportional to the density. This makes possible the continuous measurement of gas density. These systems require calibration by pure gases of different densities. The sonic restrictor (venturi) provides the reference basis. Monitoring of gas pressure, pressure differential across the flow restrictor and gas temperature in the reference chamber permits calculation of gas density by simple computer housekeeping computational and control techniques.

The system is calibrated, at the outset, by the use of pure reference gases and the basic values are stored in the aforementioned computer. That computer also relates time required for pressure change to the actual density and reads out the results in the desired format.

BRIEF DESCRIPTION OF THE DRAWINGS

My invention can best be understood by taking the description which follows in combination with the drawings herein, in which.

DETAILED DESCRIPTION OF THE PREFERRED EMBODIMENTS

Figure 1:
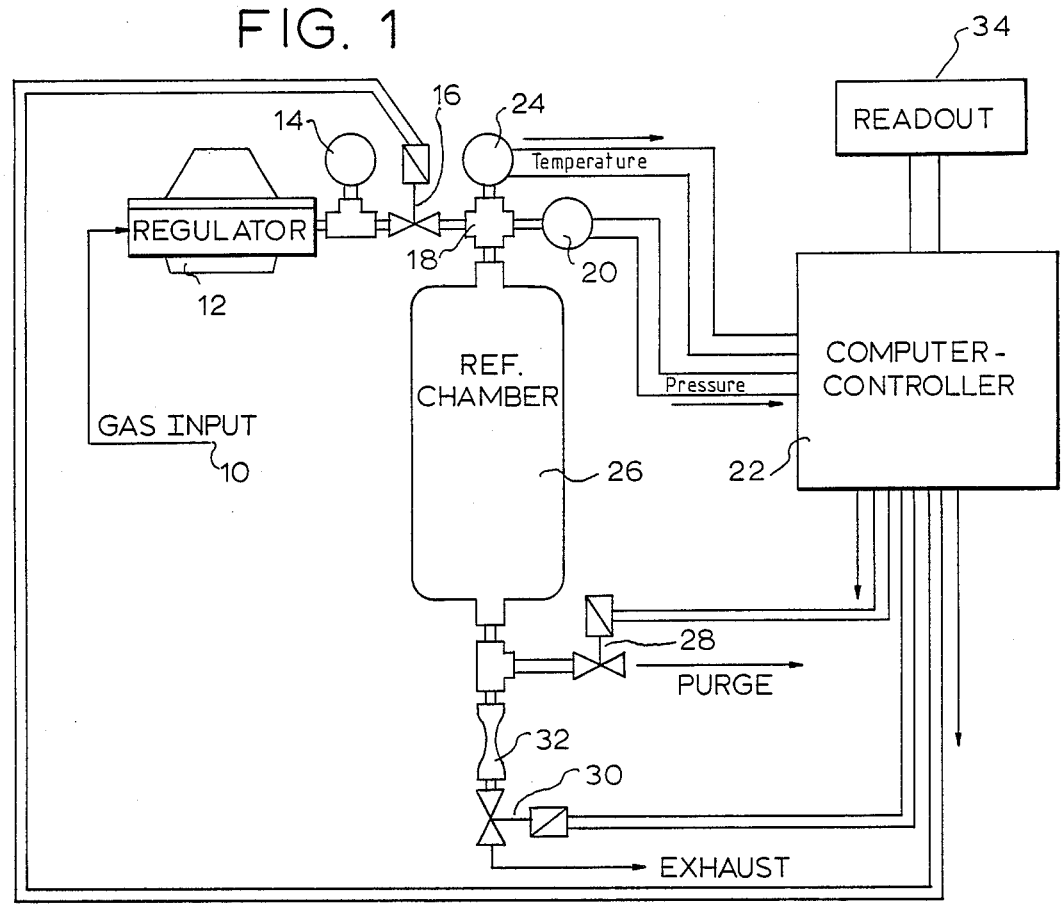
FIG. 1 is a schematic diagram of a system and apparatus for determining the density of a gas by my pressure-decay method.

In FIG. 1, gas, the density of which is to be determined, is introduced through gas input pipe 10 to regulator 12, the output of which is the object gas at a low predetermined pressure. That pressure is shown on gage 14. Computer controlled pressurizing valve 16 admits the gas at the predetermined pressure into connector 18. The pressure of the gas in that connector 18 is detected by pressure transducer 20 and that information is fed to computer-controller 22 for processing The temperature of the gas at connector 18 is detected by temperature sensor 24 and fed to computer-controller 22 for processing.

The temperature and pressure in connector 18 are, of course, the temperature and pressure of the gas in reference chamber 26, which is of known or calibrated volume. Because of the well known relationship between the temperature and the pressure of a gas, computer-controller 22 must make and does make corrections in the effective volume for any variations in the temperature reading.

Before density-determining data can be taken and processed, reference chamber 26, and the rest of the system, must be purged of any foreign gases. This is done by opening purge valve 28 and exhaust valve 30 and permitting gas to flow briefly through and out of reference chamber 26, until it is known from experience that all air has been exhausted from the system and only the object gas remains. Purge valve 28 and exhaust valve 30 may be sequenced by computer-controller 22, which performs a sequencing function as well as a data collecting and processing function.

Valves 28 and 30 are then closed until the pressure in reference chamber 26 reaches the desired initial level and valve 30 is opened the timing function commences at a predetermined pressure simultaneously with the opening of valve 30. The pressure and temperature in reference chamber 26 are then monitored, as by computer-controller 22, as the pressure decays over a convenient pressure span corresponding to that used in the initial calibration of the system. The discharge of the subject gas is through restrictor 32 which is, preferably, a 0.020 inch diameter orifice or other square-root restrictor at a sub-sonic flow rate restrictor. The time required for pressure decay in reference chamber 26 over the predetermined pressure span will be related to the density of the gas according to an empirical relationship based on calibration.

Tests using a pressure span of 4 inches of water (5" H20 to 1" H20) and a reference chamber with a volume of 0.25 cubic feet show that the time varies from 7.55 to 8.95 seconds as the specific gravity of the gas increases from 0.5 to 0.7. This amount of time difference allows acceptably accurate measurement of gas density by my declining pressure method. The time difference can be varied by changing the volume of reference chamber 26 and/or the size of restrictor 32. Computer-controller 22 has a readout 34 for plotting pressure v. time.

Figure 2:
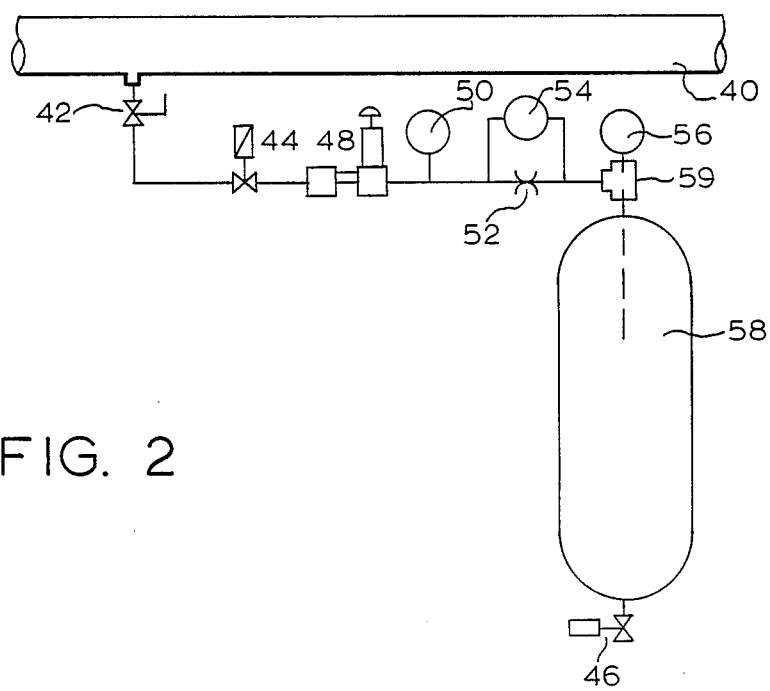
FIG. 2 is a schematic diagram of a system and apparatus for determining the density of a gas by my pressure-rise method.

Turning to FIG. 2, the correlation between gas density and rate of gas pressure change through a restrictor at a sub-sonic flow rate can be utilized when the gas pressure in a reference chamber is rising rather than decaying. In FIG. 2, gas flowing through gas pipeline 40 is introduced into my density-determining system by opening manual valve 42, electric valve 44 and exhaust valve 46 are then opened to purge and equalize reference chamber 58 with atmospheric pressure. Valve 46 is then closed. Regulator 48, which is coupled to valve 44, then provides the object gas at a pre-determined pressure level (as measured by pressure sensor or gage 50), to provide sub-sonic flow through square-root a restrictor 52, the differential pressure across which is measured by sensor or gage 54. Pressure sensor or gage 56 measures the pressure in reference chamber 58 through coupler 59. The increase in that pressure with time is measured over a predetermined pressure range corresponding to that used in calibration. The time required for the pressure to rise over that range indicates the density of the gas in pipeline 40 (based on previous gas calibration). The advantage of this system over that of FIG. 1 is that a smaller volume of purging gas is required and the density results are obtained more rapidly.

Figure 3:
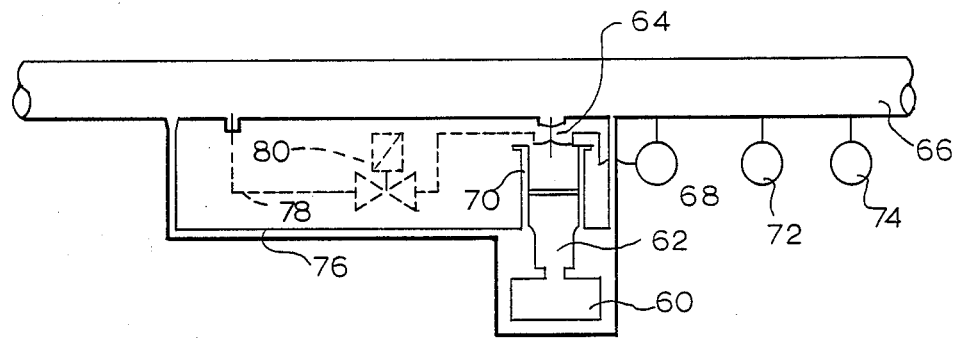
FIG. 3 is a schematic diagram of a system and apparatus for semi-continuous determination of the density of a gas at operating conditions.

In FIG. 3, gas density is determined on a semi-continuous basis. In FIG. 3, constant speed motor 60 drives piston 62 at a fixed rate so that the volume back of square-root orifice 64, which is connected directly to pipeline 66, changes constantly and at a uniform rate. The differential pressure across orifice 64, as measured by sensor or gage 68 as piston 62 moves in bellofram 70 (a combination diaphram and bellows) will vary from zero to a maximum in a cyclical way. Using the differential pressure change caused by the motion of piston 62, the density of the gas in pipeline 66 may be determined. The temperature in pipeline 66 is measured by gage or sensor 72 and the gas pressure in pipeline 66 is measured by pressure gage or sensor 74. Line 76 is a chamber balance line which protects the bellofram from high negative pressure differentials. Gas is introduced for compression into bellofram 70 through line 78 including valve 80.

Figure 4:
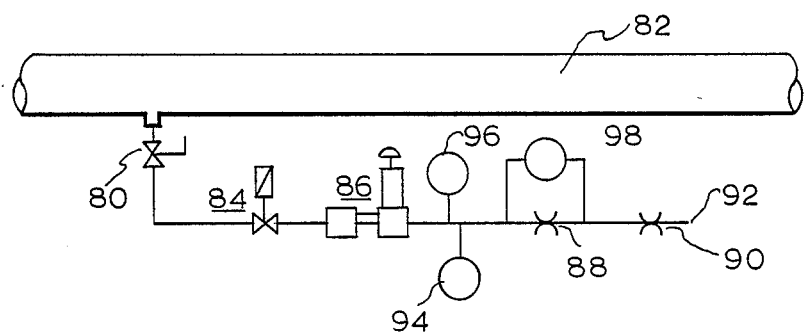
FIG. 4 is a schematic diagram of a system and apparatus for the continuous determination of the density of a gas at a pressure lower than line pressure; and, FIG. 5 is a schematic diagram of a two-chamber system for measuring gas density by a combination pressure-decay and pressure-rise method.

In FIG. 4, a system for continuous gas density measurement is disclosed.

A manual valve 80, when opened, introduces gas from pipeline 82 into the density measuring system. Valve 84 may be controlled by a computer-controller such as that shown in FIG. 1. The output of valve 84 goes to a precision pressure regulator 86, the output from which is fed to a square-root orifice 88. The output of square-root orifice 88 is fed to a sonic venturi 90 which has its output coupled to exhaust 92. The temperature of the gas going to square-root flow restrictor 88 is measured by gage or sensor 94 and the pressure of that gas is measured by pressure gage or sensor 96. The differential pressure across square-root orifice or venturi 88 is measured by gage or sensor 98.

As has been discussed, the sub-sonic mass flow of a gas through a "square-root" type of flow restrictor, such as a venturi, is a function of the square-root of the density of the gas. Mass flow through a "sonic venturi" during sonic flow responds to density in a linear manner.

By sizing sub-sonic orifice 88 and sonic orifice 90 for a predetermined flow through the sub-sonic orifice 88, which flow is equal to the sonic flow through sonic orifice 90, the differential pressure across orifice 88 will vary as a direct function of gas density. A reading of such differential pressure may be taken continuously and converted to a gas density measurement.

Figure 5:
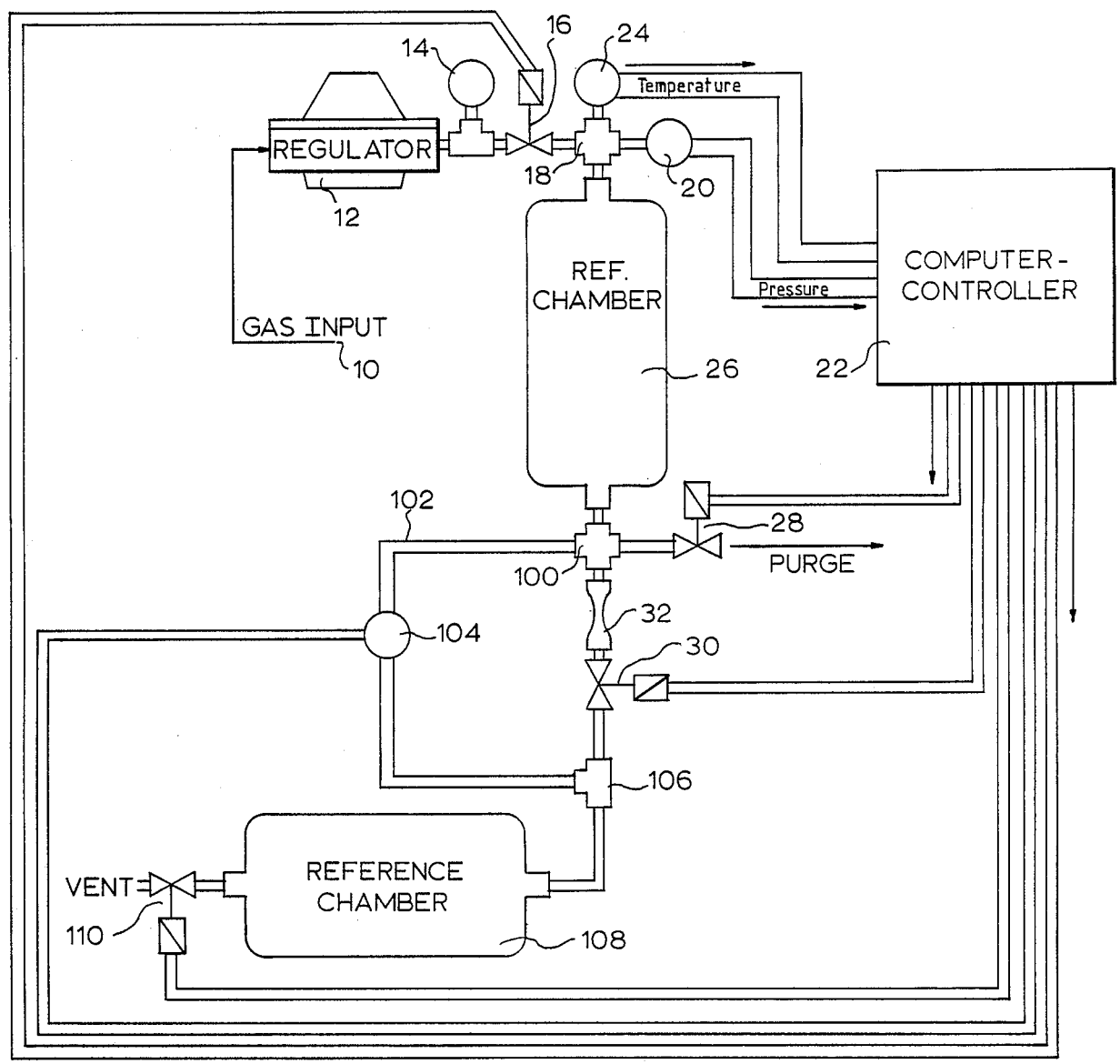

FIG. 5 shows a variation on the system of FIG. 1 in which the rate of gas pressure decay is used to determine gas density.

In FIG. 5, the system is the same as that of FIG. 1 through reference chamber 26. To the output of reference chamber 26 is connected a 4-way coupler 100 which is coupled to purge valve 28, to square-root restrictor 32 and to pressure pipe 102 which terminates in differential pressure sensor or gage 104. Restrictor or venturi 32 instead of venting to the atmosphere, as in the system of FIG. 1, is coupled through T-coupler 106 to a second chamber 108, which has an exhaust valve 110 therein. Valve 110 may be controlled by a computer-controller, such as that shown in FIG. 1. The third arm of T-coupler 106 is connected to the remaining port of differential pressure gage or sensor 104.

Reference chamber 26 is of known or calibrated volume. It is coupled, by way of sub-sonic restrictor 32, to a second chamber 108. Chamber 108 can be opened to atmosphere by opening valve 110. Gas density can then be determined by the following procedure:

Supply the object gas to input 10, as by opening a manual supply valve, not shown. Open valves 16, 28, 30 and 110 and allow chambers 26 and 108 (and the rest of the system) to purge long enough to assure a fresh sample in chamber 26. Close valves 28 and 30 and allow chamber 26 to pressurize to the desired pressure, as measured by sensor or gage 20. Close valves 16 and 110. Start the timing mechanism and open valve 30. Monitor the differential pressure at gage or sensor 104. As the differential pressure drops over the calibrated span (used for the initial calibration of the system), the time required for the differential to drop will be related to the density of the gas.

The advantages of this embodiment are:
1. Low inlet pressure
2. Lightweight construction
3. Precision pressure regulator is not required
4. Quicker determination of density than can be achieved with the system of FIG. 1, for a given precision.

While particular embodiments have been shown and described, it will be apparent to those ordinarily skilled in the art that variations and modifications may be made therein without departing from the spirit and scope of my invention.

I claim:
1. Apparatus for determining the density of a gas of unknown density, including:
a reference chamber;

a channel for gaseous communication with said reference chamber;

said channel for gaseous communication with said reference chamber including a square-root flow restrictor;

means for flowing gas at a sub-sonic rate through said square-root flow restrictor; and, timing means for measuring the time required for a predetermined change in the pressure in said reference chamber;

said apparatus having been calibrated with calibration gases of known density to correlate the time required for a given pressure change in said reference chamber and the density of the gases causing such pressure change;

said sub-sonic, square-root flow restrictor having an input port and an output port and said output port being coupled to a sonic restrictor;

whereby the density of an object gas of unknown density may be determined by comparing the time required for a given pressure change in said reference chamber produced by the object gas with the time required for an identical pressure change in said reference chamber with each of said calibration gases.

2. Apparatus according to claim 1 in which the size of the sub-sonic, square-root restrictor and the size of the sonic restrictor are such that the mass flow through the sub-sonic, square-root flow restrictor and the mass sonic flow through the sonic restrictor are equal.

3. Apparatus for determining the density of a gas of unknown density, including:

a reference chamber;

a channel for gaseous communication with said reference chamber;

said channel for gaseous communication with said reference chamber including a square-root flow restrictor;

means for flowing gas at a subsonic rate through said square-root flow restrictor; and timing means for measuring the time required for a predetermined change in the pressure in said reference chamber;

said apparatus having been calibrated with calibration gases of known density to correlate the time required for a given pressure change in said reference chamber and the density of the gases causing such pressure change;

said means for flowing gas including piston means for forcing gas through said square-root flow restrictor;

said piston means moving at a constant rate of speed;

whereby the density of an object gas of unknown density may be determined by comparing the time required for a given pressure change in said reference chamber produced by the object gas with the time required for an identical pressure change in said reference chamber with each of said calibration gases.

* * * * *